United States Patent

Groke et al.

[11] Patent Number: 6,048,987
[45] Date of Patent: Apr. 11, 2000

[54] PROCESS FOR PRODUCING COATED CATALYSTS FOR THE SYNTHESIS OF MALEIC ANHYDRIDE BY GAS-PHASE OXIDATION

[75] Inventors: Dirk Groke, Taufkirchen; Christoph Ruedinger, München; Hans-Juergen Eberle, München; Reinhard Jering, München; Richard Bosch, Germering, all of Germany

[73] Assignee: Consortium für Elektrochemische Industrie GmbH, Munich, Germany

[21] Appl. No.: 09/103,237

[22] Filed: Jun. 23, 1998

[30] Foreign Application Priority Data

Jun. 26, 1997 [DE] Germany ............ 197 27 235

[51] Int. Cl.⁷ .................. C07D 307/34; B01J 27/198
[52] U.S. Cl. .................. 549/260; 549/259; 549/260
[58] Field of Search .................. 549/259, 260; 502/209

[56] References Cited

U.S. PATENT DOCUMENTS

| | | | |
|---|---|---|---|
| 3,987,063 | 10/1976 | Lemal et al. | 549/260 |
| 4,132,670 | 1/1979 | Katsumoto et al. | 549/259 |
| 4,336,198 | 6/1982 | Dolhyj et al. | 549/260 |
| 5,288,880 | 2/1994 | Matsuura | 549/260 |
| 5,496,787 | 3/1996 | Hatano et al. | 502/209 |

FOREIGN PATENT DOCUMENTS

| | | |
|---|---|---|
| 0072381 | 2/1983 | European Pat. Off. |
| 2245651 | 4/1975 | France . |
| 19645066 | 10/1996 | Germany . |
| 9300166 | 1/1993 | WIPO . |
| 9625230 | 8/1996 | WIPO . |

OTHER PUBLICATIONS

Derwent Abstract corresponding to DE 19645066 (# 98–262308).

*Primary Examiner*—Bernard Dentz
*Attorney, Agent, or Firm*—Collard & Roe, P.C.

[57] ABSTRACT

There is a process for producing coated catalysts for the gas-phase oxidation of $C_4$ hydrocarbons to maleic anhydride. A vanadyl phosphate catalyst precursor is prepared having a V/P ratio of from 1:0.5 to 1:2 and a mean vanadium oxidation state of from 3.9 to 4.5. The vanadyl phosphate precursor is then calcined by heating for a several hours at a temperature of from 200° C. to 500° C. before being applied, in an aqueous suspension to the support bodies. Furthermore, there is the use of these coated catalysts in processes for the gas-phase oxidation of saturated or unsaturated $C_4$-hydrocarbons to maleic anhydride.

11 Claims, No Drawings

PROCESS FOR PRODUCING COATED CATALYSTS FOR THE SYNTHESIS OF MALEIC ANHYDRIDE BY GAS-PHASE OXIDATION

BACKGROUND OF THE INVENTION

1. Field of the Invention

The invention relates to a process for producing coated catalysts for the gas-phase oxidation of $C_4$-hydrocarbons to maleic anhydride, and also the use of these coated catalysts in processes for the gas-phase oxidation of saturated or unsaturated $C_4$-hydrocarbons to maleic anhydride.

2. The Prior Art

The preparation of maleic anhydride (=MA) from $C_4$-hydrocarbons by means of catalytic gas-phase oxidation has been known for about 20 years. Catalysts based on vanadyl phosphates (vanadyl pyrophosphate, vanadium-phosphorus oxides) are used in this process. The preparation of these vanadyl phosphates proceeds via a catalyst precursor which is obtainable by two reaction routes. The first is preparation in an aqueous medium; the second is preparation in organic solvents. The precursor is then, in a second step before or after shaping, converted into the actual catalytically active substance either in the reactor (in situ) or externally.

The reaction of the $C_4$-hydrocarbon in contact with the catalyst is carried out in various types of reactors. Examples include fixed-bed, fluidized-bed and also riser reactors, always using the abovementioned catalysts. For fixed-bed reactors, use is made of unsupported catalysts, i.e. catalysts which consist exclusively of the catalytically active component. These unsupported catalysts have the disadvantage that large amounts of active material have to be used. Due to the usually compact form of the shaped bodies, there is a high pressure drop in industrial reactors, which leads to increased energy consumption. These disadvantages can be overcome by the use of coated catalysts. Furthermore, the smaller amount of material in the case of coated catalysts results in a significantly reduced local temperature increase in the catalyst. This has a positive influence on the selectivity of the catalyst. Since the active component of a coated catalyst is present only in the outer shell on an inert support, there is a significant reduction in the amount of material required. Selection of catalyst supports having a suitable shape (e.g. rings) reduces the pressure build-up in the reactor. This reduces the power required for the gas blower.

EP-A 72381 describes a process for producing a coated catalyst for the gas-phase oxidation of $C_4$-hydrocarbons to MA. To prepare the precursor, a solution of $V_2O_5$, uranyl acetate and $H_3PO_4$ in isobutanol is heated in the presence of hydrogen chloride. The resulting precursor is isolated by distilling off water and isobutanol. After drying, the uncalcined precursor is applied to inert supports. The application is carried out by moistening the inert support material with water in a first step. Subsequently the precursor is applied, possibly in small amounts, if necessary with further addition of water, without use of a binder. Due to the initial moistening of the support with water, a porous material having a certain water absorbency is used. According to this document, contents of applied material of from 50 to 80% by weight, based on the weight of the coated shaped body, are necessary for producing usable catalysts. The activation or calcination of the material obtained in this way is carried out at a temperature of 400° C. for 16 hours in air after application of the precursor to the support body. Due to the application of the uncalcined precursor in aqueous medium, the catalyst activity is unsatisfactory.

WO-A 96/25230 describes a process for producing coated catalysts for the synthesis of MA, in which the precursor is not mixed with water. Instead the precursor is mixed with an organic solvent and optionally with a binder and is then applied to the support. Finally, the supported catalyst is converted into the catalytically active form by calcination. This calcination can be carried out either in the reactor (in situ) or externally. The catalyst produced in this way contains from 0.02 g/cm³ to 0.4 g/cm³ (bulk volume) of active component. The thickness of the active component layer is from 0.1 mm to 0.8 mm. It was found that application of the uncalcined precursor in an organic solvent gives more active supported catalysts than when the application is carried out in an aqueous suspension. However, a disadvantage is that use of an organic solvent leads to problems because of the explosion risk posed by air/solvent mixtures formed during evaporation.

SUMMARY OF THE INVENTION

It is therefore an object of the invention to provide a process for producing a coated catalyst for the synthesis of maleic anhydride by gas-phase oxidation. By this process, the application of the precursor in organic solvents can be avoided without causing a reduction in activity when the application is carried out in an aqueous suspension. Also, an increase in yield can be achieved.

The invention provides a process for producing coated catalysts for the gas-phase oxidation of $C_4$-hydrocarbons to maleic anhydride, in which a vanadyl phosphate precursor having a V/P ratio of from 1:0.5 to 1:2 and a mean vanadium oxidation state of from 3.9 to 4.5 is prepared in an aqueous or organic medium. This precursor is dried. The vanadyl phosphate precursor is then calcined by heating for several hours at a temperature of from 200° C. to 500° C. The calcined material is then applied in an aqueous suspension to the support bodies.

The precursor can be prepared in a manner known per se, for example by the method described in U.S. Pat. No. 4,132,670, EP-A 72,381 or DE-A 19,645,066. The disclosure of each document is herewith incorporated by reference. For this purpose, a vanadium(V) compound is reduced with a reducing agent in an aqueous or organic medium in the presence of a phosphorus(V) compound. Suitable vanadium(V) compounds are, for example, vanadium pentoxide, vanadium oxide halides such as $VOCl_3$, vanadium phosphates, ammonium metavanadate, vanadium pentahalides such as $VCl_5$. Vanadium pentoxide is preferred. Suitable phosphorus compounds are phosphorus(V) compounds such as phosphoric acid, phosphorus pentoxide, phosphorus pentachloride or phosphorus perhalides. Phosphoric acid is preferred.

The vanadium(V) compound and the phosphorus (V) compound are used in a V/P atom ratio of from 1:0.5 to 1:2, preferably from 1:0.9 to 1:1.3. The molar ratio of reducing agent to vanadium(V) compound is from 1:1 to 2:1, preferably from 1:1 to 1.5:1.

When the precursor is prepared in an organic medium, it is preferred to use an organic solvent having a reducing action, preferably isobutanol. If desired, additional reducing agents such as benzyl alcohol, phosphorus acid or hydrogen chloride are added. To reduce the vanadium, the vanadium (V) compound, preferably vanadium pentoxide, is suspended in the organic medium, for example isobutanol, preferably in admixture with a reducing agent, for example benzyl alcohol. After addition of the phosphorus(V) compound, for example orthophosphoric acid, the mixture is heated under reflux for several hours, preferably from 2 to 20 hours. The water of reaction formed during this procedure can be removed as an azeotrope. After the reduction is complete, the organic medium is removed, for example by distillation, and the precursor is dried.

The preparation of the precursor in an aqueous medium is carried out analogously. The vanadium(V) compound, preferably vanadium pentoxide, is mixed with the phosphorus (V) compound, preferably orthophosphoric acid, and the reducing agent, preferably oxalic acid. This mixture is heated under reflux for several hours, preferably from 2 to 20 hours. After the reduction is complete, the water is removed, for example by distillation, and the precursor is dried.

After the reduction, the vanadyl phosphate precursor has a V/P ratio of from 1:0.5 to 1:2 and a mean vanadium oxidation state of from 3.9 to 4.5. The precursor can be calcined in the form of the dried powder. Alternatively it can be shaped into tablets or granules and then calcined.

The precursor is activated in a manner known per se by oxidative calcination, for example using the methods described in WO-A 93/00166 or DE-A 19645066. The disclosure of each document is herewith incorporated by reference. In the oxidative calcination, the precursor is, for example, heated in air at a temperature of usually from 200° C. to 500° C. in a forced air furnace. The heating time is several hours, generally from 2 to 20 hours. In another embodiment the calcination can be carried out stepwise using different heating steps and in the presence of different atmospheres, for example an inert gas, preferably nitrogen or water vapor.

To coat the support bodies, the calcined vanadyl phosphate is suspended in water. If necessary, an additional mechanical comminution step can be carried out. Inert fillers can be added to the suspension as diluents to control the activity of the finished catalyst. The inert fillers can also be added to the dried precursor powder before calcination. Suitable diluents are, for example, $SiO_2$, $TiO_2$, SiC and graphite. If inert fillers are added, their proportion is generally from 0.5 to 25% by weight, based on the calcined precursor.

If desired, promoters in the form of their water-soluble compounds, e.g. as chlorides, carbonates, hydroxides or nitrates, can also be added to the suspension. Alternatively, the promoters can be added during the preparation of the precursor, for example during or after the reduction. Promoter elements which can be used are, for example: Li, Fe, Mo, Cr, Ce, Zr, Co, Zn, U, Bi. The promoters are preferably added in such amounts that the atom ratios of the individual promoters to V range from 0.01:1 to 0.1:1. It is also possible to use combinations of promoters and in this case the atom ratio of the sum of the elements used to vanadium should range from 0.01:1 to 0.1:1.

Uniform distribution of the constituents of the suspension is provided by thorough mixing of the suspension. The viscosity of the suspension has to be matched to the requirements of the coating apparatus. An organic binder, advantageously in the form of an aqueous dispersion, is then added to the suspension obtained. Suitable binders are known to those skilled in the art. Preferred binders include polyvinyl alcohol, polyvinyl acetate or copolymers of vinyl acetate with vinyl laurate, ethylene or acrylates, and also polyacrylates. The binder is added in an amount which ensures sufficient adhesion of the coating to the support. A sufficient amount of binder ranges of from 10 to 20% by weight of binder, based on the solids content of the suspension.

Varying the content of organic binder influences the porosity of the coating after removal of the binder in the reactor. Thus increasing the binder content, increases the porosity due to the burning out of the binder under the reaction conditions. If desired, further organic compounds such as polyethylene glycols or stearic acid can be added to promote pore formation.

Suitable support materials are, for example, aluminum oxide, aluminates, silicon carbide, silicon oxide, silicates, steatite, duranite, porcelain or stoneware. In principle, the supports can have any shape and surface structure. Preference is given to regularly shaped, mechanically stable bodies such as spheres, rings, or saddles. Other examples include supports having a honeycomb structure or which are provided with channels, or include other shaped bodies known from the prior art. However, to obtain a low back-pressure throughout the catalyst bed in the reactor, it is preferable to use structures such as rings having a proportion of open volume which is as high as possible.

The dimensions of the support bodies are determined primarily by the dimensions of the reactor in which the catalysts are used. In MA production, tube reactors or multitube reactors are generally used. The dimensions of the support bodies are therefore determined by the internal diameter of the reaction tubes and should be from ½ to $\frac{1}{10}$ of the internal diameter. It is preferred to use spheres having a diameter of from 3 to 10 mm. Also preferred are rings having a height of from 3 to 10 mm, an external diameter of from 4 to 10 mm and a wall thickness of from 1 to 2 mm.

The coating of the supports can be carried out in a known manner. After placing the supports in the coating apparatus, for example a spray coater or coating drum, the support bodies are heated to the temperature necessary for coating. In general this temperature is from 50° C. to 100° C., to ensure evaporation of the water added to the slurry. The application of the active component can be carried out continuously or batchwise. Continuous application is preferred. Because water is used as suspension medium, it is not necessary to protect against explosion. Also, the disposal of organic solvents is not necessary.

The calcined precursor, if desired in admixture with promoters and diluents, is applied to the support bodies. The application is in such an amount that the proportion by weight of the active component is from 20 to 80% by weight, based on the total weight of the coated support. After application of the active component, the resulting shaped bodies can be introduced directly into a reactor for the conversion of the $C_4$-hydrocarbons into MA.

The invention further provides for the use of the coated catalysts produced according to the invention in processes for the gas-phase oxidation of saturated or unsaturated $C_4$-hydrocarbons to maleic anhydride.

In the preparation of MA, the $C_4$-hydrocarbon is reacted with an oxygen-containing gas in the presence of the catalyst produced according to the invention, preferably in fixed-bed reactors. Customary fixed-bed reactors are, for example, reaction tubes which are combined to form multitube reactors and are surrounded by a heat exchange medium. The reaction tubes are arranged vertically and the reaction mixture flows through them. They are made of a material which is inert toward the heat exchange medium, catalyst, starting materials and products. The reaction tubes may be made of steel, and generally have a length of from 2000 mm to 6000 mm, an internal diameter of from 10 mm to 30 mm and a wall thickness of from 1 mm to 4 mm. Useful heat exchange media include eutectic salt mixtures, for example a chloridefree melt of potassium nitrate and sodium nitrite. The catalyst is introduced into the reaction tubes from the top. The catalyst is held in place by holding devices fitted into the vicinity of the lower ends of the tubes.

Suitable starting materials are saturated or unsaturated $C_4$-hydrocarbons or mixtures thereof, for example n-butane, 1-butene, 2-butene (cis and trans) and 1,3-butadiene. It is preferred to use n-butane. However, other hydrocarbons containing at least four adjoining carbon atoms can also be used, for example pentane or (cyclo)pentenes. The reaction gas usually comprises a gas mixture of oxygen-containing gas, preferably air, and $C_4$-hydrocarbon. The proportion of hydrocarbon in the mixture can be from 0.5 to 10% by volume, preferably from 1 to 3% by volume. The reaction temperature is generally from 300° C. to 500° C. The reaction gas mixture flows vertically through the reaction tubes in which the desired reaction proceeds exothermically. The flow rate of the gaseous reaction mixture is designed so that the volume of gas passed through the reactor per hour is from 500 to 4000 times the volume of catalyst (GHSV (gas hourly space velocity)=500–4000 $h^{-1}$). The reaction products leave the reactor and are removed from the reaction gas stream by means of downstream retention systems such as scrubbers, or condensers. By-products obtained in addition to the desired product MA are predominantly CO, $CO_2$ and traces of acetic and acrylic acids. The crude product is worked up by suitable methods (e.g. distillation).

In a preferred embodiment, the reactor charged with the catalyst produced according to the invention is started up at a temperature of from 250° C. to 400° C. using oxygen-containing gas mixtures, preferably at a temperature of from 300° C. to 350° C. The oxygen-containing gas mixture used can for example, be air. Also possible for use is a butane/air mixture having a butane concentration in a range from 0.25% by volume to 2.0% by volume, preferably from 0.5% by volume to 1.5% by volume. The flow rate of the gas mixture should be from 500 to 4000 $h^{-1}$ (i.e. 1 of gas mixture/h/l of catalyst charge). This start-up phase generally takes a few hours, preferably from 0.5 to 2 hours. The reaction can subsequently be continued under the above-mentioned reaction conditions customary in MA production.

In the method according to the invention for producing the coated catalyst, the use of water is found to have no adverse effects on the catalytic activity of the catalyst. This is contrary to the adverse effects that were observed when using the uncalcined precursor according to WO-A 96/25230. At the same time, the advantages which result from the application of the active components in an aqueous medium to the support bodies are retained. The use of water as suspension medium significantly simplifies handling during the application procedure. The risk of explosion, as is the case when using organic solvents, can be eliminated. At the same time, the use of water as suspension medium leads to a reduction in costs and avoids pollution of the environment. It is not necessary to dispose of or to incinerate the solvent vapors obtained in the processes known from the prior art.

Furthermore, it is found when using the processes known from the prior art that the coating of the support with uncalcined material has a substantial detrimental effect on the adhesion of the active component to the support during the calcination required. This leads to a lower mechanical stability of the coating after calcination. This makes the filling of the reaction tubes with the binder-free catalyst more difficult because of the high level of abrasion. Also this can lead to problems in reactor operation caused by increased pressure build-up. Use of the process of the invention overcomes these disadvantages. This is because the calcination is carried out before application of the active component. The binder is therefore still present when introducing the catalyst into the reactor.

It has also been found, particularly surprisingly, that the mechanical stability of the coating is significantly increased by the method used according to the invention even after removal of the binder during the synthesis of MA. Thus, good adhesion of the active composition to the inert support material is ensured over the entire operating time. In addition, emptying of the reactors is also made easier. In contrast to the catalyst of the invention, a great amount of dust is formed in the case of the catalysts produced according to the prior art as a result of abrasion of the coating.

Other objects and features of the present invention will become apparent from the following detailed description considered in connection with the accompanying examples which disclose several embodiments of the present invention. It should be understood, however, that the examples are designed for the purpose of illustration only and not as a definition of the limits of the invention.

DETAILED DESCRIPTION OF THE PREFERRED EMBODIMENT

Test for Determining the Mechanical Strength of the Coating of Coated Catalysts

The stability of the coating was determined for the coated shaped bodies with and without binder by means of the following experimental procedure:

20 g of the coated shaped bodies were poured into a vertically clamped glass tube having an internal diameter of 22 mm and a length of 90 cm. The lower end of the glass tube was closed flush by means of a glass beaker. Depending on adhesion, part of the coating chipped off from the shaped bodies as a result of the impact. The weight loss of the shaped bodies was determined by carefully separating off the chipped-off material. This weight loss was employed as a measure of the stability or adhesion of the coating (% by weight abrasion). The numerical measure reported was the proportion of active component, based on the original amount, which had become detached from the support during the test.

Determination of the Catalytic Properties of Coated Catalysts

The catalytic testing of the catalysts was carried out in the following way:

In an electrically heated tube furnace, shaped catalyst bodies were introduced into a quartz tube (internal diameter: 19 mm) to form an 11 cm long bed (bed volume: 31.2 ml). The weight of catalyst introduced was recorded. In addition, a thermocouple (Ni—CrNi) was placed in the bed to make it possible to measure the reaction temperature. A rotameter or a mass flow regulator (Brooks, model: 5850E) was utilized for metering in the gases air and butane. The experiments were carried out using 600 $ml_{STP}$/min of air and 5 $ml_{STP}$/min of n-butane, corresponding to a butane concentration of 0.83% by volume, and a gas flow rate of 1165 $h^{-1}$ ($ml_{STP}$=gas volume at STP, viz. 0° C., 1 bar, in ml). The maleic anhydride formed was collected in a water-filled wash bottle over a known period of time and determined titrimetrically by titration with 0.1 N NaOH using phenolphthalein as indicator. By means of appropriate switching of valves, both the inlet gas mixture and the waste gas after removal of the condensable materials could be analyzed using a flame ionization detector (=FID, modified Hewlett Packard HP 5890 II gas chromatograph) and the conversion could thus be determined. The yield was then calculated from the amount of MA formed per unit time and the amount of butane.

Conversion, yield and selectivity are obtained from the following relationships:

Conversion C [%]=Int(in,C$_4$)−Int(out,C$_4$)/Int(in,C$_4$)

Yield Y [mol%]=n(out,MA)/n(in,C$_4$)=0.5×consumption of (0.1N NaOH/ml)/v(in,C$_4$)×t Selectivity S[%]=Y/C Explanations of the symbols used:
Int(in/out, X): intensity of FID signal at inlet or outlet
n(in/out, X): number of mol of the component X at the inlet or outlet
v(in,C$_4$): gas flow of n-butane in mol/h=c(in,C$_4$)×v(in, total)
C(in,C$_4$)=0.83% by volume
v(in,total)=27 mmol/h=605 ml$_{STP}$/h
t: reaction time in h Since the volume change during the reaction is in the region of a few percent, the yield calculation can be carried out according to the above equation. Any by-products formed and their concentration can be determined by analysis of the scrubbing water by means of ion chromatography. During the test runs, care was taken to ensure that the bed temperature did not exceed 480° C., since otherwise there was a risk of damaging the catalyst. To assess the catalysts, the temperature of the furnace was varied until the maximum yield was obtained. The temperature and the conversion at maximum yield were noted.

Production of the Coated Catalysts

EXAMPLE 1
Production of a Coated MA Catalyst According to the Invention

A mixture of 967 ml (770 g) of isobutanol and 107 ml (112 g) of benzyl alcohol were admixed cold with 100 g of vanadium pentoxide while stirring. The mixture was heated to reflux temperature (107° C.) and held under these conditions for 3 hours. After cooling the mixture by 20° C., 121.8 g of 106% strength phosphoric acid were added and the mixture was subsequently reheated to reflux. After a further reflux time of 16 hours, the mixture was cooled to about 50° C. and filtered. The resultant blue filter cake was dried at 150° C. for 10 hours and pressed to form pellets.

To carry out the calcination, the pellets were placed in a tube furnace. Before commencement of the heating procedure, the furnace was supplied with a gas mixture of 50% nitrogen/50% air. The furnace temperature was then increased while keeping the gas flow constant, so that a temperature of 150° C. was reached after 4 hours. The gas composition was then changed so as to give a gas mixture consisting of 50% air and 50% steam. The temperature was then increased to 420° C. over a period of 10 hours and was held at this temperature for 4 hours. After the hold time, the calcined precursor was cooled to room temperature under nitrogen.

800 g of the calcined precursor were admixed with 2 l of deionized water and stirred overnight. The resulting suspension was transferred to a glass vessel, admixed with 269 g of a polyvinyl acetate dispersion (solids content: 50%), made up to 3.5 l and mixed thoroughly by stirring for a period of 1 hour and passed through a 0.5 mm sieve.

After charging the coating machine (from Glatt, type Uniglatt) with 800 g of supports (4 mm steatite spheres) and heating it to operating temperature, the suspension was sprayed onto the supports over a period of 4 hours. After cooling the supports to room temperature, they were taken out.

1762 g of coated catalyst were obtained (catalyst I). The amount of active component applied was determined by reweighing after oxidative removal of the binder. In the above experiment, an active component (=active composition) content of 50% by weight was found. The abrasion resistance and the catalytic data were determined by the above method and are summarized in Table 1.

EXAMPLE 2
Production of a Coated MA Catalyst According to the Invention (Modified Proportion of Active Component)

375 g of a precursor calcined in pellet form as described in Example 1 were admixed with 1 l of deionized water and stirred overnight. The resulting suspension was transferred to a glass vessel, admixed with 126 g of a polyvinyl acetate dispersion (solids content: 50%), made up to 2 l and mixed thoroughly by stirring for a period of 1 hour and passed through a 0.5 mm sieve.

After charging the coating machine (from Glatt, type Uniglatt) with 1 kg of supports (4 mm steatite spheres) and heating it to operating temperature, the suspension was sprayed onto the supports over a period of 2 hours. After application of the total amount of suspension, the apparatus was rinsed with water to remove any residual suspension remaining in the feed lines. After cooling the supports to room temperature, they were taken out.

1454 g of coated supports were obtained (catalyst II). The amount of active component applied was determined by a method similar to Example 1. An active component (=active composition) content of 27.0% by weight was found. The testing of the catalyst and the determination of the mechanical properties were carried out as described above. The results are shown in Table 1.

EXAMPLE 3 (COMPARATIVE)
Production of Coated MA Catalysts using the Method of WO-A 96/25230

The preparation of the vanadyl phosphate precursor was, as regards the reduction and drying steps, carried out using a method similar to Example 1.

To produce the coated catalysts, 200 g of the support (4 mm steatite spheres) were placed in a rotating cylindrical container and heated to 50° C. by means of a warm air stream. A suspension of 200 g of catalyst precursor in 300 g of isobutanol was prepared and applied to the surface of the supports by means of a spray gun. The coated catalyst was then subjected to calcination in a subsequent step.

The calcination was carried out using a procedure similar to Example 1, except that the tube furnace was charged with coated support bodies.

The resulting catalyst (catalyst III) was tested for its catalytic performance under the above-described conditions. The test results are summarized in Table 1. The mechanical stability of the coating was likewise determined for the uncalcined, calcined and used catalyst by the above method. The data are likewise shown in Table 1.

EXAMPLE 4 (Comparative)

Production of a Coated MA Catalyst using the Method Described in EP-A 72381

The preparation of the vanadyl phosphate precursor was, as regards the reduction and drying steps, carried out by a method similar to Example 1. To coat the supports with a proportion of active component of 50% by weight, based on the weight of the coated supports, 50 g of steatite spheres (4 mm diameter) were mixed with 5 g of distilled water in a cylindrical glass vessel. After the water had been distributed on the support, 50 g of the precursor were added in 5 portions. After addition of each 10 g, the apparatus was kept in motion for a further 10 minutes in each case. After addition of the second portion, another 4 g of water was added and allowed to act for another 10 minutes. The third portion of precursor was then added. After a further 15 minutes, which were necessary for the powder to be completely taken up by the supports, the fourth and fifth portion of precursor were applied with water being sprayed on in between. Uptake of the fourth precursor portion took 30 minutes and uptake of the fifth portion took 40 minutes. The uniformly coated supports were dried at 110° C. for 16 hours and subsequently calcined using a method similar to that described in Example 1, except that the tube furnace was charged with coated support bodies.

The catalytic performance and the mechanical stability of the catalyst (catalyst IV) were measured by the above methods. All measurement data are shown in Table 1.

EXAMPLE 5

Use of Promoters in the Production of Coated Catalysts as Described in Example 1 (Production According to the Invention)

a.) 500 g (=3.25 mol of V) of calcined precursor which had been prepared by a method similar to Example 1 were suspended in 750 ml of water. 12.74 g (=0.065 mol of Mo) of ammonium molybdate $((NH_4)_2MoO_4)$ were added to the mixture; after this had dissolved, the mixture was admixed with 233.1 g of polyvinyl acetate dispersion (solids content: 50%), mixed thoroughly and made up to a total volume of 3 l. The suspension was applied to inert supports (4 mm steatite spheres). The coating process was similar to that described in Example 1.

b.) 500 g (=3.25 mol of V) of calcined precursor which had been prepared using a method similar to Example 1 were suspended in 750 ml of water. 4.8 g (=0.065 mol of Li) of lithium carbonate $(Li_2CO_3)$ were added to the mixture and the mixture was admixed with 233.1 g of polyvinyl acetate dispersion using a method similar to a.) and made up to 3 l. The coating process was carried out by a method similar to Example 1 using 4 mm steatite spheres.

c.) 500 g (=3.25 mol of V) of calcined precursor which had been prepared using a method similar to Example 1 were suspended in 750 ml of water. 18.9 g (=0.065 mol of Co) of cobalt nitrate $(Co(NO_3)_2.6\ H_2O)$ were added to the mixture and the mixture was admixed with 233.1 g of polyvinyl acetate dispersion using a method similar to a.) and made up to 3 l. The coating process was carried out as described in Example 1 using 4 mm steatite spheres.

d.) 500 g (=3.25 mol of V) of calcined precursor which had been prepared using a method similar to Example 1 were suspended in 750 ml of water. 26.0 g (=0.065 mol of Cr) of chromium(III) nitrate $(Cr(NO_3)_3.9\ H_2O)$ were added to the mixture and the mixture was admixed with 233.1 g of polyvinyl acetate dispersion using a method similar to a.) and made up to 3 l. The coating process was carried out as described in Example 1 using 4 mm steatite spheres.

e.) 500 g (=3.25 mol of V) of calcined precursor which had been prepared using a method similar to Example 1 were suspended in 750 ml of water. 14.3 g (=0.065 mol of Zn) of zinc acetate $(Zn(CH_3COO)_2.2\ H_2O)$ were added to the mixture and the mixture was admixed with 233.1 g of polyvinyl acetate dispersion using a method similar to a.) and made up to 3 l. The coating process was carried out as described in Example 1 using 4 mm steatite spheres.

EXAMPLE 6

Use of Diluents in the Production of Coated MA Catalysts as Described in Example 1 (According to the Invention)

A suspension was prepared from 500 g of calcined precursor, 100 g of titanium dioxide (BET surface area: 8 m/g and 233.1 g of polyvinyl acetate dispersion. The total volume of the suspension was 3 l. The coating process was carried out as described in Example 1 using 4 mm steatite spheres.

Interpretation of the Results

Comparison of the mechanical stability of the various catalysts clearly shows that the catalysts produced by the process of the invention are superior, both before and after use, to the catalysts produced by known methods. In the case of the catalysts produced by conventional methods, from 12.5% by weight to 20% by weight of the active component is lost in the calcined state before use, while no abrasion was found in the case of the catalysts produced according to the invention. After use in the reactor, the abrasion formed was from 12% by weight to 27% by weight for the previously known production processes compared to from 0 to 3% by weight in the case of the samples produced according to the invention.

To compare the catalytic performance, the catalysts I and IV or II and III have to be compared to one another. They are grouped in this way because the activity of the catalysts is dependent on the amount of active component. A meaningful comparison can therefore only be made between catalysts having a similar content of active component. In the case of the catalysts containing 50% by weight of active composition, the system produced according to the invention gives a significantly higher yield than the catalyst IV produced by the aqueous coating methods as described in EP-A 72381 (I: 53 mol% yield; IV: 42 mol% yield). The poor performance of the catalyst IV is also reflected in the high furnace temperature combined with a low conversion.

Comparison of the catalysts II and III shows the superiority of the production process of the invention compared to the process of WO-A 96/25230 (coating procedure using organic solvents). Here too, the significantly increased activity, the higher conversion and the lower abrasion of the system according to the invention are apparent.

In summary, the experiments carried out show that the production process of the invention is significantly superior to the previously known methods of producing coated catalysts for the oxidation of $C_4$-hydrocarbons to MA. These superior results are with respect to the mechanical stability of the catalyst as well as for the catalytic performance of the catalyst.

TABLE 1

Performance data and mechanical stability of the coated MA catalysts

| Catalyst | Active Composition % by weight | Active Composition g/cm$^1$ of bed | Furnace temperature (° C.) | Performance data Conversion (%) | Performance data Yield (mol %) | Abrasion (% by weight) Fresh | Abrasion (% by weight) Calcined | Abrasion (% by weight) Used |
|---|---|---|---|---|---|---|---|---|
| I (According to the invention) | 50 | 0.41 | 350 | 85.7 | 52.9 | Not applicable | 0 | 3 |
| II (According to the invention) | 27 | 0.26 | 360 | 94.6 | 56.3 | Not applicable | 0 | 0 |
| III (Comparison) | 25 | 0.20 | 370 | 85.6 | 50.9 | 4 | 12.5 | 27 |
| IV (Comparison) | 50 | 0.50 | 400 | 73.9 | 42.2 | 1 | 20.2 | 11.7 |

While a few embodiments of the present invention have been shown and described, it is to be understood that many changes and modifications may be made thereunto without departing from the spirit and scope of the invention as defined in the appended claims.

What is claimed is:

1. Process for producing coated catalysts for the gas-phase oxidation of $C_4$-hydrocarbons to maleic anhydride consisting essentially of preparing a vanadyl phosphate precursor having a V/P ratio of from 1:0.5 to 1:2 and a mean vanadium oxidation state of from 3.9 to 4.5 in a liquid selected from the group consisting of an aqueous liquid and an organic liquid;

drying said vanadyl phosphate precursor;

calcining the vanadyl phosphate precursor by heating for several hours at a temperature of from 200° C. to 500° C., to produce a calcined precursor; and applying the calcined precursor in an aqueous suspension to support bodies to produce the coated catalysts.

2. The process as claimed in claim 1, comprising preparing a promoter mixture of the calcined vanadyl phosphate precursor with at least one promoter selected from the group consisting of a water-soluble compound of Li, Fe, Mo, Cr, Ce, Zr, Co, Zn, U, Bi; and applying said promoter mixture to the support bodies.

3. The process as claimed in claim 1, comprising, preparing a diluent mixture of the calcined vanadyl phosphate precursor with at least one diluent selected from the group consisting of $SiO_2$, $TiO_2$, SiC and graphite; and applying said diluent mixture to the support bodies.

4. The process as claimed in claim 1, comprising preparing a binder mixture of the calcined vanadyl phosphate precursor with an organic binder; and applying said binder mixture to the support bodies.

5. The process as claimed in claim 4, wherein said binder mixture comprises the calcined vanadyl phosphate precursor with an organic binder selected from the group consisting of polyethylene glycol and stearic acid.

6. The process as claimed in claim 1, comprising applying the calcined vanadyl phosphate precursor to the support bodies in an amount such that the proportion by weight of active component is from 20% to 80% by weight, based on the total weight of coated support.

7. A coated catalyst for the gas-phase oxidation of $C_4$-hydrocarbons to maleic anhydride prepared by a process as claimed in claim 1.

8. A process for a gas-phase oxidation of a substance selected from the group consisting of a saturated $C_4$-hydrocarbon, an unsaturated $C_4$-hydrocarbon and the mixtures thereof, to produce maleic anhydride consisting essentially of the steps of preparing a calcined vanadyl phosphate precursor;

applying the calcined precursor in an aqueous suspension to support bodies to produce a coated catalyst, having a volume;

charging said coated catalyst into a reactor;

preparing a reaction gas mixture comprising a $C_4$-hydrocarbon and an oxygen-containing gas;

passing said reaction gas mixture of $C_4$-hydrocarbon with said oxygen-containing gas through said reactor charged with said coated catalyst, the proportion of hydrocarbon in said reaction gas mixture being from 0.5 to 3.0% by volume at a reaction temperature of from 300° C. to 500° C.; and passing a volume of the reaction gas mixture through the reactor per hour at a rate of from 500 to 4000 times the volume of the catalyst.

9. The process as claimed in claim 8, comprising starting up the reactor charged with the catalyst in a preceding step at a temperature ranging from 300° C. to 350° C. using oxygen-containing reaction gas mixture.

10. The process as claimed in claim 9, wherein the oxygen-containing reaction gas mixture used is air.

11. The process as claimed in claim 9.

wherein the oxygen-containing reaction gas mixture used is a butane/air mixture having a butane concentration in a range from 0.25% by volume to 2.0% by volume.

* * * * *